(12) United States Patent
Younes et al.

(10) Patent No.: US 10,106,430 B2
(45) Date of Patent: Oct. 23, 2018

(54) OXYCOMBUSTION SYSTEMS AND METHODS WITH THERMALLY INTEGRATED AMMONIA SYNTHESIS

(71) Applicant: Saudi Arabian Oil Company, Dhahran (SA)

(72) Inventors: Mourad Younes, Dhahran (SA); Tidjani Niass, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 204 days.

(21) Appl. No.: 14/143,737

(22) Filed: Dec. 30, 2013

(65) Prior Publication Data
US 2015/0183650 A1 Jul. 2, 2015

(51) Int. Cl.
*B01J 8/04* (2006.01)
*C01C 1/04* (2006.01)
(Continued)

(52) U.S. Cl.
CPC .............. *C01C 1/0417* (2013.01); *B01J 12/00* (2013.01); *C01C 1/0488* (2013.01);
(Continued)

(58) Field of Classification Search
CPC .................. B01J 8/04; C01C 1/04; F02C 6/00
(Continued)

(56) References Cited

U.S. PATENT DOCUMENTS 2,087,325 A * 7/1937 Lawrence et al. ............ 423/396
3,851,046 A 11/1974 Wright et al.
(Continued)

FOREIGN PATENT DOCUMENTS

BG 103061 A 8/1999
DE 102011016759 A1 10/2012
(Continued)

OTHER PUBLICATIONS

International Search Report and Written Opinion dated Mar. 3, 2015 pertaining to International Patent Application PCT/US2014/068036.
(Continued)

*Primary Examiner* — Huy Tram Nguyen
(74) *Attorney, Agent, or Firm* — Dinsmore & Shohl LLP

(57) ABSTRACT

Oxycombustion systems and oxycombustion methods include thermally integrated ammonia synthesis. The oxycombustion systems may include an air separation unit that separates air into an oxygen stream and a nitrogen stream. An ammonia synthesis unit synthesizes ammonia from a hydrogen feed and the nitrogen stream to form a crude ammonia stream. An ammonia separation unit condenses the crude ammonia stream and separates the ammonia from any unreacted nitrogen and hydrogen to form a purified ammonia stream. An oxycombustion reactor combusts a fuel from a fuel feed stream in the presence of the oxygen stream from the air separation unit to generate hot water or steam. At least one thermal integration may be present in the oxycombustion systems and may be chosen from a reactor thermal linkage of the ammonia synthesis unit with the oxycombustion reactor, a separator thermal linkage of the air separation unit with the ammonia separation unit, or both.

8 Claims, 3 Drawing Sheets

(51) Int. Cl.
  *F02C 6/00* (2006.01)
  *C07C 273/10* (2006.01)
  *B01J 12/00* (2006.01)
  *C07C 273/04* (2006.01)
  *F23L 7/00* (2006.01)
  *B01D 53/14* (2006.01)

(52) U.S. Cl.
  CPC .......... *C07C 273/04* (2013.01); *C07C 273/10* (2013.01); *F23L 7/007* (2013.01); *B01D 53/1418* (2013.01); *B01D 2256/22* (2013.01); *Y02E 20/344* (2013.01); *Y02P 20/129* (2015.11); *Y02P 20/52* (2015.11)

(58) Field of Classification Search
  USPC .................... 422/148; 95/46; 60/780, 783
  See application file for complete search history.

(56) References Cited

U.S. PATENT DOCUMENTS

| | | | |
|---|---|---|---|
| 4,273,743 A * | 6/1981 | Barber et al. | 422/148 |
| 4,867,959 A | 9/1989 | Grotz | |
| 5,118,481 A * | 6/1992 | Lyon | 423/235 |
| 5,695,616 A | 12/1997 | Helfritch et al. | |
| 5,724,805 A * | 3/1998 | Golomb | F01K 23/106 |
| | | | 60/39.12 |
| 6,448,441 B1 | 9/2002 | Wing-Chiu et al. | |
| 6,632,846 B2 * | 10/2003 | Sheppard et al. | 518/715 |
| 8,323,602 B2 | 12/2012 | Wright et al. | |
| 8,537,961 B2 * | 9/2013 | Keller | F01K 3/181 |
| | | | 290/52 |
| 2002/0004612 A1 * | 1/2002 | Fukunaka | B01D 5/0012 |
| | | | 564/67 |
| 2002/0053436 A1 * | 5/2002 | Vinegar | C09K 8/592 |
| | | | 166/302 |
| 2002/0174659 A1 * | 11/2002 | Viteri | H01M 8/04022 |
| | | | 60/780 |
| 2008/0223077 A1 * | 9/2008 | Prosser et al. | 62/646 |
| 2009/0178408 A1 * | 7/2009 | Brugerolle | F25J 3/0406 |
| | | | 60/645 |
| 2010/0018218 A1 * | 1/2010 | Riley et al. | 60/783 |
| 2011/0250119 A1 * | 10/2011 | Mello | C01B 3/34 |
| | | | 423/359 |
| 2012/0100062 A1 * | 4/2012 | Nakamura et al. | 423/359 |
| 2012/0213690 A1 | 8/2012 | Petrocelli et al. | |
| 2012/0301834 A1 * | 11/2012 | Clements | F23J 15/06 |
| | | | 431/2 |
| 2013/0000352 A1 * | 1/2013 | Gonzalez Salazar | F25J 3/04084 |
| | | | 62/649 |
| 2013/0108534 A1 | 5/2013 | Ostuni et al. | |

FOREIGN PATENT DOCUMENTS

| | | |
|---|---|---|
| EP | 0818232 B1 | 6/2006 |
| EP | 2156878 A1 | 2/2010 |
| EP | 2 589 426 A1 | 5/2013 |
| WO | 2012/177137 A1 | 12/2012 |
| WO | 2013/095130 A1 | 6/2013 |
| WO | 2013/108191 A1 | 7/2013 |

OTHER PUBLICATIONS

International Preliminary Report on Patentability dated Jul. 5, 2016 pertaining to International Application No. PCT/US2014/068036.

* cited by examiner

OXYCOMBUSTION SYSTEMS AND METHODS WITH THERMALLY INTEGRATED AMMONIA SYNTHESIS

BACKGROUND

Field

The present specification generally relates to combustion systems and, more particularly, to oxycombustion systems and methods in which oxycombustion is conducted together with a thermally integrated ammonia synthesis.

Technical Background

In a carbon-constrained world, energy efficiency and $CO_2$ capture play major roles in controlling $CO_2$ emissions for a sustainable future. The growing worldwide demand for energy is constantly in strife with pushes for protection of the environment. This combination of issues requires ongoing development of systems that are not only energy efficient but also reduce emissions of $CO_2$ and pollutants. Energy efficient systems are most often the fruit of systems integration and energy fluxes management.

Oxycombustion with $CO_2$ capture is a technique to combust fuels with pure oxygen while capturing $CO_2$ and avoiding numerous pollutants. Oxycombustion uses substantially pure oxygen to combust a fuel, leaving the flue gases substantially nitrogen-free, with primarily $CO_2$ and water as waste products or flue gases. It is then possible to cool the flue gases to condense the water and recover the $CO_2$ stream with minimum energy penalty. Typical combustion processes in the presence of nitrogen molecules and oxygen molecules generate nitrogen oxides ($NO_x$), the harmful pollutants that have led to emissions legislation around the world.

Most fossil fuels also contain sulfur compounds that lead to the formation of sulfur oxide ($SO_x$) pollutants when these fuels are combusted or oxidized. In refinery streams, hydrogen produced in the refineries can be used to hydro-treat liquid fuels, for example, and reduce sulfur content. Several processes also exist for post-combustion $SO_x$ removal. For example, ammonia injection into a flue gas stream has been found to reduce both $NO_x$ and $SO_x$ emissions. Nevertheless, in such post-combustion processes the ammonia must be purchased or derived from a separate source at a both an energy cost and a monetary cost.

Ongoing needs exist for fuel combustion systems that operate with increased energy efficiency and that produce fewer harmful emissions of greenhouse gases such as $CO_2$ and pollutants such as $NO_x$, and/or $SO_x$.

SUMMARY

According to various embodiments, oxycombustion systems with thermally integrated ammonia synthesis are provided. The oxycombustion systems may include an air separation unit that separates an air feed stream into an oxygen stream and a nitrogen stream. The oxycombustion systems may also include an ammonia synthesis unit that synthesizes ammonia from a hydrogen feed stream and the nitrogen stream from the air separation unit to form a crude ammonia stream containing the ammonia and, optionally, unreacted nitrogen and hydrogen. The oxycombustion systems may further include an ammonia separation unit that condenses the crude ammonia stream formed in the ammonia synthesis unit and separates the ammonia from any unreacted nitrogen and hydrogen to form a purified ammonia stream. The oxycombustion systems may further include an oxycombustion reactor that combusts a fuel from a fuel feed stream in the presence of the oxygen stream from the air separation unit to generate combustion heat. In some embodiments, at least one thermal integration is present in the oxycombustion systems. The at least one thermal integration may be chosen from a reactor thermal linkage of the ammonia synthesis unit with the oxycombustion reactor, a separator thermal linkage of the air separation unit with the ammonia separation unit, or both.

According to further embodiments, methods for performing oxycombustion with thermally integrated ammonia synthesis are provided. The methods may include separating an air feed stream with an air separation unit into an oxygen stream and a nitrogen stream. The oxygen stream may be flowed to an oxycombustion reactor, and the nitrogen stream may be flowed to an ammonia synthesis unit. The nitrogen stream in the ammonia synthesis unit may be combined with a hydrogen feed stream to synthesize ammonia and form a crude ammonia stream containing the ammonia and, optionally, unreacted nitrogen or hydrogen. The crude ammonia stream may be condensed in an ammonia separation unit so as to separate the ammonia in the crude ammonia stream from any unreacted nitrogen or hydrogen in the crude ammonia stream and form a purified ammonia stream. The methods may further include combining a fuel from a fuel stream with the oxygen stream from the air separation unit to form a fuel mixture. The fuel mixture may be combusted in the oxycombustion reactor to generate combustion heat. The methods may further include transferring thermal energy through at least one thermal integration while the fuel mixture is being combusted and the ammonia is being synthesized. The at least one thermal integration may be chosen from a reactor thermal linkage of the ammonia synthesis unit with the oxycombustion reactor, a separator thermal linkage of the air separation unit with the ammonia separation unit, or both.

Additional features and advantages of the embodiments described herein will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Figure 1:
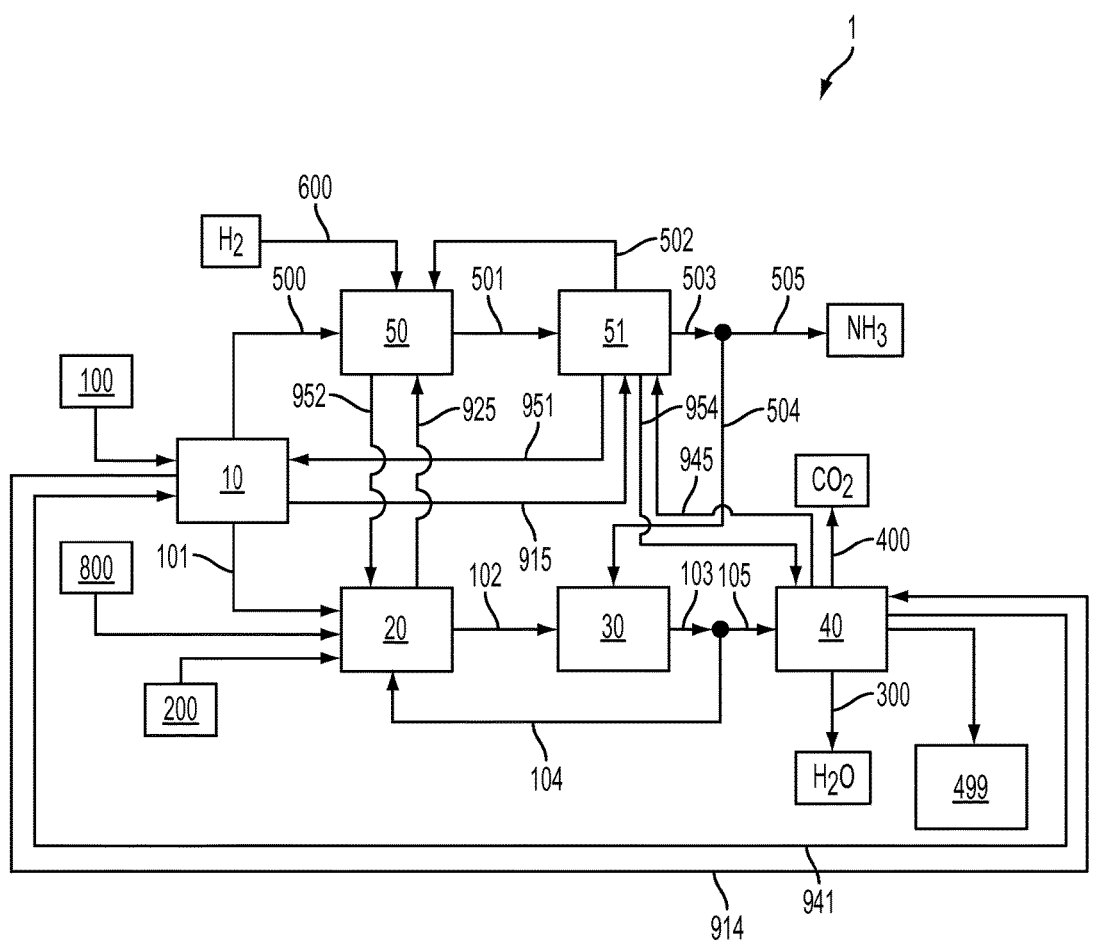
FIG. 1 is a schematic representation of an oxycombustion system with thermally integrated ammonia synthesis, according to embodiments described herein.

Embodiments of oxycombustion systems with thermally integrated ammonia synthesis will now be described with reference to FIGS. 1-3. According to some embodiments, the oxycombustion systems 1, 2, 3 may include an air separation unit 10 that separates an air feed stream 100 into an oxygen stream 101 and a nitrogen stream 500. The oxycombustion systems 1, 2, 3 may also include an ammonia synthesis unit 50 that synthesizes ammonia from a hydrogen feed stream 600 and the nitrogen stream 500 from the air separation unit 10 to form a crude ammonia stream 501 containing the ammonia and, optionally, unreacted nitrogen and hydrogen. The oxycombustion systems 1, 2, 3 may further include an ammonia separation unit 51 that condenses the crude ammonia stream 501 formed in the ammonia synthesis unit 50 and separates the ammonia from any unreacted nitrogen and hydrogen to form a purified ammonia stream 503. The oxycombustion systems 1, 2, 3 may further include an oxycombustion reactor 20 that combusts a fuel from a fuel feed stream 200 in the presence of the oxygen stream 101 from the air separation unit 10 to generate combustion heat that may be used to heat water and form hot water or steam, for example. In some embodiments, at least one thermal integration is present in the oxycombustion systems. The at least one thermal integration may be chosen from a reactor thermal linkage 925, 952 of the ammonia synthesis unit 50 with the oxycombustion reactor 20, a separator thermal linkage 915, 951 of the air separation unit 10 with the ammonia separation unit 51, or both.

One embodiment of an oxycombustion system is provided in FIG. 1. An air separation unit 10 separates an air feed stream 100 into an oxygen stream 101 and a nitrogen stream 500. The air separation unit 10 may include any type of apparatus capable of separating nitrogen and oxygen components of air into separate streams, such as the oxygen stream 101 and the nitrogen stream 500. For example, the air separation unit 10 may contain a cryogenic distillation apparatus, in which air is cooled until liquefied and the components of the air such as oxygen, nitrogen, and other minor components such as inert gases and carbon dioxide are selectively distilled. Generally, cryogenic distillation apparatus require a refrigeration cycle, whereby thermal energy or heat must be removed from the air and rejected away from the apparatus. Other classes of separation apparatus not involving liquefaction of the air, such as those employing pressure-swing adsorption, vacuum-swing adsorption, or membrane technologies may also be used as the air separation unit 10. The thermodynamics of the processes used by such types of separation apparatus also involve rejection of heat. The oxygen stream 101 leaving the air separation unit 10 is enriched in oxygen, in that it has a higher volume content of oxygen than that of air, which contains about 21% oxygen by volume. In some exemplary embodiments, the oxygen stream 101 may contain greater than 25% by volume $O_2$, greater than 40% by volume $O_2$, greater than 50% by volume $O_2$, greater than 60% by volume $O_2$, greater than 70% by volume $O_2$, or greater than 75% by volume $O_2$. In further exemplary embodiments, the oxygen stream 101 may be pure oxygen or substantially pure oxygen, such as from 80% to 100% by volume $O_2$, 90% to 100% by volume $O_2$, 95% to 100% by volume $O_2$, or 95% to 99.9% by volume $O_2$, for example. The precise oxygen content of the oxygen stream 101 may be adjustable based on the operating parameters and configuration of the air separation unit 10 and may also be chosen based on the operational needs of the oxycombustion reactor 20. Optionally, an atomization medium may be added from an atomization source 800 to the oxygen stream 101 at the oxycombustion reactor 20, such as into a chamber of the oxycombustion reactor 20 that includes the burner for combusting the fuel. In one embodiment, the atomization medium may include steam or carbon dioxide, for example. Atomization media may facilitate more complete and more efficient combustion of the fuel in the oxycombustion reactor 20. The nitrogen stream 500 leaving the air separation unit 10 may be pure nitrogen or substantially pure nitrogen, such as from such as from 80% to 100% by volume $N_2$, 90% to 100% by volume $N_2$, 95% to 100% by volume $N_2$, or 95% to 99.9% by volume $N_2$, for example.

The ammonia synthesis unit 50 may be any industrial-scale apparatus or vessel that synthesizes ammonia from hydrogen and nitrogen using the Haber process, a modified Haber process, or any other industrial ammonia synthesis process. According to the Haber process, ammonia synthesis from hydrogen and nitrogen may be conducted at high pressure (15 MPa to 25 MPa, for example) and high temperature (300° C. to 550° C., for example) over one or more catalyst beds. The hydrogen of the hydrogen feed source 600 may be supplied from an independent source or may be derived from petroleum-related processes in other parts of a refinery where the oxycombustion system 1 is being used. The conversion reaction of hydrogen and nitrogen to ammonia is exothermic, and heat is generated in the reactor bed. Nevertheless, an initial heat is required to heat the nitrogen and the hydrogen to the reaction temperature. A single pass of the hydrogen from the hydrogen feed source 600 and the nitrogen from the nitrogen stream 500 through the ammonia synthesis unit 50 does not typically result in full conversion of the source gases to ammonia. As such, a crude ammonia stream 501 is formed that is fed to the ammonia separation unit 51. The crude ammonia stream 501 contains ammonia, unreacted nitrogen and/or hydrogen, and potentially small amounts of other gases derived from air that may be present in the nitrogen stream 500.

The ammonia separation unit 51 condenses at least a portion of the crude ammonia stream 501 formed in the ammonia synthesis unit 50, separates the ammonia from any unreacted nitrogen and hydrogen or other gases present in the crude ammonia stream 501, and directs the ammonia into a purified ammonia stream 503. In some embodiments, the ammonia separation unit 51 condenses only the ammonia in the crude ammonia stream 501. Because of the low conversion rate of the ammonia synthesis reaction, the crude ammonia stream 501 is cooled to below the boiling point of ammonia (about −33° C.) to condense and recover liquid ammonia, whereupon the hydrogen, nitrogen, and/or other components of the crude ammonia stream 501 that remain in the gaseous state may be recirculated through recirculation line 502 back to the ammonia synthesis unit 50 to increase the overall conversion rate. To condense the ammonia, a cold sink is required to remove heat from the crude ammonia stream 501 in the ammonia separation unit 51. In some embodiments, the purified ammonia stream 503 may be split into an ammonia recovery stream 505 and an ammonia scrubbing stream 504. The ammonia in the ammonia recovery stream 505 may be collected or used for any further purpose outside the oxycombustion system 1. The ammonia in the ammonia scrubbing stream 504 may be used to remove pollutants from flue gases, as will be described in greater detail below. In other embodiments, the purified ammonia stream 503 may not be split and may be used exclusively for collection through the ammonia recovery stream 505 or exclusively for scrubbing of flue gas through the ammonia scrubbing stream 504.

The oxycombustion reactor 20 combusts a fuel from a fuel feed stream 200 in the presence of the oxygen stream 101 from the air separation unit 10 to generate combustion heat. The oxycombustion reactor 20 may be any apparatus suitable for combusting the fuel at the temperatures reached when the fuel is burned in pure oxygen or substantially pure oxygen. In exemplary embodiments, the fuel may be any type of fossil fuel, such as natural gas, for example, or any type of combustible biomass. Combustion of the fuel in enriched oxygen, for example in an oxygen stream 101 having an oxygen content by volume greater than that of air (about 21 vol. %), in pure oxygen, or in substantially pure oxygen typically generates fewer pollutants, with $CO_2$ and $H_2O$ being the primary components of flue gases. Also, because nitrogen is absent or substantially absent from the combustion gases, $NO_x$ pollutants are severely reduced. In some embodiments, the oxycombustion reactor 20 may be a boiler, such that the combustion heat generated by the combustion of the fuel may be used to heat or vaporize a fluid such as water, for example. Hot or vaporized liquid (such as hot water or steam, for example) may then be used to transfer the combustion heat elsewhere outside the oxycombustion system 1, to provide energy to a power generation system such as a turbine, for example, or to provide a thermal integration for the oxycombustion system 1 itself, as will be discussed in greater detail below.

The oxycombustion system 1 further includes at least one thermal integration. As described above, various operations in the oxycombustion system 1 either produce heat or require heat. For example, the combustion of the fuel in the oxycombustion reactor 20 produces a substantial amount of heat. On the other hand, the synthesis of ammonia in the ammonia synthesis unit 50 requires heat to raise the nitrogen and hydrogen to reaction temperature. Likewise, the separation of air in the air separation unit 10 may involve warming liquid air from a temperature lower than the boiling point of liquid nitrogen (78 K; −195° C.) during a distillation process. On the other hand, the condensation of ammonia from the crude ammonia stream 501 in the ammonia separation unit 51 requires a rejection of heat from the crude ammonia stream 501 to lower the temperature of the crude ammonia stream 501 to below the boiling point of ammonia (about −33° C.). The at least one thermal integration of the oxycombustion system 1 takes advantage of the thermal needs of the various components of the oxycombustion system 1 to allow one component with excess heat to provide the excess heat to a component that needs additional heat or, in another sense, to allow one component that is already cold to help another hot component become colder or to allow one component that is already hot to help another colder component become hotter.

In some embodiments, the at least one thermal integration of the oxycombustion system 1 may include a reactor thermal linkage 925, 952 of the ammonia synthesis unit 50 with the oxycombustion reactor 20. The reactor thermal linkage 925, 952 may be configured as any industrially feasible mechanism for establishing thermal communication between the ammonia synthesis unit 50 and the oxycombustion reactor 20. In particular, the reactor thermal linkage provides a mechanism for directing combustion heat produced by the oxycombustion reactor 20 during combustion of the fuel toward the ammonia synthesis unit 50, which requires the heat to bring the nitrogen from the nitrogen stream 500 and the hydrogen from the hydrogen feed stream 600 up to a temperature suitable for conducting ammonia synthesis. In some embodiments, the reactor thermal linkage 925, 952 of the ammonia synthesis unit 50 with the oxycombustion reactor 20 may be a boiler loop that transfers heat to the ammonia synthesis unit 50. The combustion heat going into the boiler loop may be obtained from the oxycombustion reactor 20 itself (such as from a chamber in the oxycombustion reactor 20), from flue gas formed in the oxycombustion reactor 20, from at least a portion of any hot water or steam heated by the oxycombustion reactor 20, or a combination thereof. The boiler loop may contain a heat transfer fluid such as water, for example, that accepts heat from the oxycombustion reactor 20 then rejects the heat to the ammonia synthesis unit 50. Thermal transfer to and from the boiler loop may be accomplished by any practical means such as through heat exchanger fins or coils. The heat transfer fluid in the boiler loop may be circulated within the boiler loop by any practical means, such as with a pump, for example.

In some embodiments, the at least one thermal integration of the oxycombustion system 1 may include a separator thermal linkage 915, 951 of the air separation unit 10 with the ammonia separation unit 51. The separator thermal linkage 915, 951 may be configured as any industrially feasible mechanism for establishing thermal communication between the air separation unit 10 and the ammonia separation unit 51. In particular, the separator thermal linkage provides a mechanism for directing heat away from the ammonia separation unit 51 while ammonia is being condensed from the crude ammonia stream 501. The transfer of heat in this manner is facilitated by the significantly lower temperature of the liquefied air being separated in the air separation unit 10. Thus, in such embodiments, the air separation unit 10 becomes a cold sink for the ammonia separation unit 51. In some embodiments, the separator thermal linkage 915, 951 of the air separation unit 10 and the ammonia separation unit 51 may be a separator loop that removes heat from the ammonia separation unit 51. Thereby, heat from the ammonia separation unit 51 enters the separator loop to be rejected at the air separation unit 10. The separator loop may contain a heat transfer fluid having an appropriately low freezing point, whereby the heat transfer fluid can accept the heat from the ammonia separation unit 51 and reject the heat at the air separation unit 10. Thermal transfer to and from the separator loop may be accomplished by any practical means such as through heat exchanger fins or coils. The heat transfer fluid in the separator loop may be circulated within the separator loop by any practical means, such as with a pump, for example.

In some embodiments, the at least one thermal integration of the oxycombustion system 1 may include both a reactor thermal linkage 925, 952 of the ammonia synthesis unit 50 with the oxycombustion reactor 20, as described above, and a separator thermal linkage 915, 951 of the air separation unit 10 with the ammonia separation unit 51, as described above.

In addition to the air separation unit 10, oxycombustion reactor 20, the ammonia synthesis unit 50, and the ammonia separation unit 51, the oxycombustion system 1 according to some embodiments may also include a flue-gas treatment system 30 that treats a flue gas formed by the combustion of the fuel in the oxycombustion reactor 20. The flue gas may exit the oxycombustion reactor 20 through flue gas stream 102. Depending on the type of fuel being combusted in the oxycombustion reactor 20, and also depending on the types of impurities that may be present in the fuel or the oxygen stream 101, the flue gas stream 102 may contain various pollutants such as particulates, $NO_x$ and $SO_x$ gases, or heavy metals. These pollutants are preferably scrubbed from the flue gas stream to avoid their release into the atmosphere or environment. In some embodiments, the purified ammonia stream 503 may be in fluidic communication with the flue-gas treatment system 30, and at least a portion of the ammonia separated in the ammonia separation unit 51 may be used in the flue-gas treatment system 30 to remove pollutants from the flue gas. To use the ammonia in the flue-gas treatment system 30, the purified ammonia stream 503 may be split to include the ammonia scrubbing stream 504, which may be directed to the flue-gas treatment system 30. The ammonia from the ammonia scrubbing stream 504 may then be used in processes such as selective catalytic reduction (SCR) or electron-beam flue-gas treatment (EB-FGT) to remove $NO_x$ species from the flue gas. Example systems for removing pollutants such as $NO_x$, $SO_x$, and heavy metals from flue gases in general are described in U.S. Pat. Nos. 8,323,602 and 5,695,616, and in European Patents EP2156878 and EP0818232.

The flue gas treated in the flue-gas treatment system 30 may leave the flue-gas treatment system 30 through a scrubbed stream 103. The scrubbed stream 103 may contain carbon dioxide ($CO_2$), water, and possibly also may contain nitrogen and inert gases. In such cases, the $CO_2$ leaves the oxycombustion reactor 20 in the flue gas stream 102 and, in turn, the flue-gas treatment system 30 outputs the $CO_2$. In some embodiments, the scrubbed stream 103 may simply be exhausted to the atmosphere. In other embodiments, the scrubbed stream 103 may be directed through a capture stream 105 into a carbon dioxide capture unit 40. In other embodiments, the scrubbed stream may be directed into a reactor recirculation stream 104 that adds the components of the scrubbed stream 103 (such as $CO_2$ and water, for example) back into the oxycombustion reactor 20 to moderate the combustion temperature of the fuel. In other embodiments, the scrubbed stream 103 may be split such that a first portion of the scrubbed stream 103 flows into the capture stream 105 for $CO_2$ capture in the carbon dioxide capture unit 40, while a second portion of the scrubbed stream 103 flows into the reactor recirculation stream 104.

In the carbon dioxide capture unit 40, if one is present in the oxycombustion system 1, the capture stream 105 may be treated by cooling, for example, to separate the carbon dioxide in the capture stream 105 from any additional components of the capture stream 105 such as water, for example. In exemplary embodiments, the carbon dioxide may be captured in a gaseous state, while the water is condensed out in a liquid state. The carbon dioxide may then be recovered from a carbon dioxide recovery stream 400 for further uses inside or outside the oxycombustion system 1, and the water may be released or reused from water recovery stream 300. For example, in one embodiment the carbon dioxide recovered from the carbon dioxide recovery stream 400 may be reused inside the oxycombustion system 1 as an atomizing medium to be introduced into the oxycombustion reactor 20 via the atomization source 800. Any additional gases that remain in the capture stream 105 after passing through the carbon dioxide capture unit 40, typically only nitrogen and noble gases such as argon, may be vented from the oxycombustion system 1 through a system exhaust 499. It should be understood that the oxycombustion system 1 of FIG. 1 may additionally require the implementation of process apparatus such as compressors, recirculation fans, pumps, and controllers using configurations that should be readily apparent to those having ordinary skill in the art, even though they may not be explicitly shown in FIG. 1.

In some embodiments, when the carbon dioxide capture unit 40 is included in the oxycombustion system 1, the oxycombustion system 1 may further include at least one capture-unit thermal integration. As noted above, the carbon dioxide capture unit 40 may be operated by cooling flue gases to low temperatures to condense water from the carbon dioxide recovery stream 400. For example, the flue gases may be cooled to temperatures such as from −30° C. to −55° C., depending on the initial concentration of $CO_2$ in the carbon dioxide recovery stream 400, on the types of and amounts of expected impurities that may be present in the carbon dioxide recovery stream 400, and also on a desired purity of any $CO_2$ to be recovered and put to use inside or outside the oxycombustion system 1. As such, the carbon dioxide capture unit 40 may be utilized as a cold sink for other components of the oxycombustion system 1. In some exemplary embodiments, the oxycombustion system 1 may include an air-separator capture-unit thermal linkage 914, 941 between the carbon dioxide capture unit 40 and the air separation unit 10 as a capture-unit thermal integration. In other exemplary embodiments, the oxycombustion system 1 may include an ammonia-separator capture-unit thermal linkage 956, 965 between the carbon dioxide capture unit 40 and the ammonia separation unit 51 as a capture-unit thermal integration. In still other exemplary embodiments, the oxycombustion system 1 may include both an air-separator capture-unit thermal linkage 914, 941 and an ammonia-separator capture-unit thermal linkage 956, 965 as capture-unit thermal integrations.

When present, the at least one capture-unit thermal integration such as the air-separator capture-unit thermal linkage 914, 941, the ammonia-separator capture-unit thermal linkage 945, 954, or both, may be configured as any industrially feasible mechanism for establishing thermal communication between the carbon dioxide capture unit 40 and the air separation unit 10 or the ammonia separation unit 51, as applicable. In particular, the air-separator capture-unit thermal linkage 914, 941 may provide a mechanism for directing heat away from the air separation unit 10 while air is being condensed from air feed stream 100. Likewise, the ammonia-separator capture-unit thermal linkage 945, 954 may provide a mechanism for directing heat away from the ammonia separation unit 51 while ammonia is being condensed from the crude ammonia stream 501. In both the air-separator capture-unit thermal linkage 914, 941 and the ammonia-separator capture-unit thermal linkage 945, 954, the transfer of heat is facilitated by the significantly lower temperature of the carbon dioxide being condensed in the carbon dioxide capture unit 40. Thus, with capture-unit thermal integrations, the carbon dioxide capture unit 40 becomes a cold sink for the air separation unit 10 or the ammonia separation unit 51. The at least one capture-unit thermal integration may be configured as any industrially feasible thermal-transfer loop that can bring about the desired transfer of heat. Such a thermal-transfer loop may contain a heat transfer fluid having an appropriately low freezing point, for example. Thermal transfer to and from the thermal-transfer loop may be accomplished by any practical means such as through heat exchanger fins or coils. The heat transfer fluid in the separator loop may be circulated within the thermal-transfer loop by any practical means, such as with a pump, for example.

Figure 2:
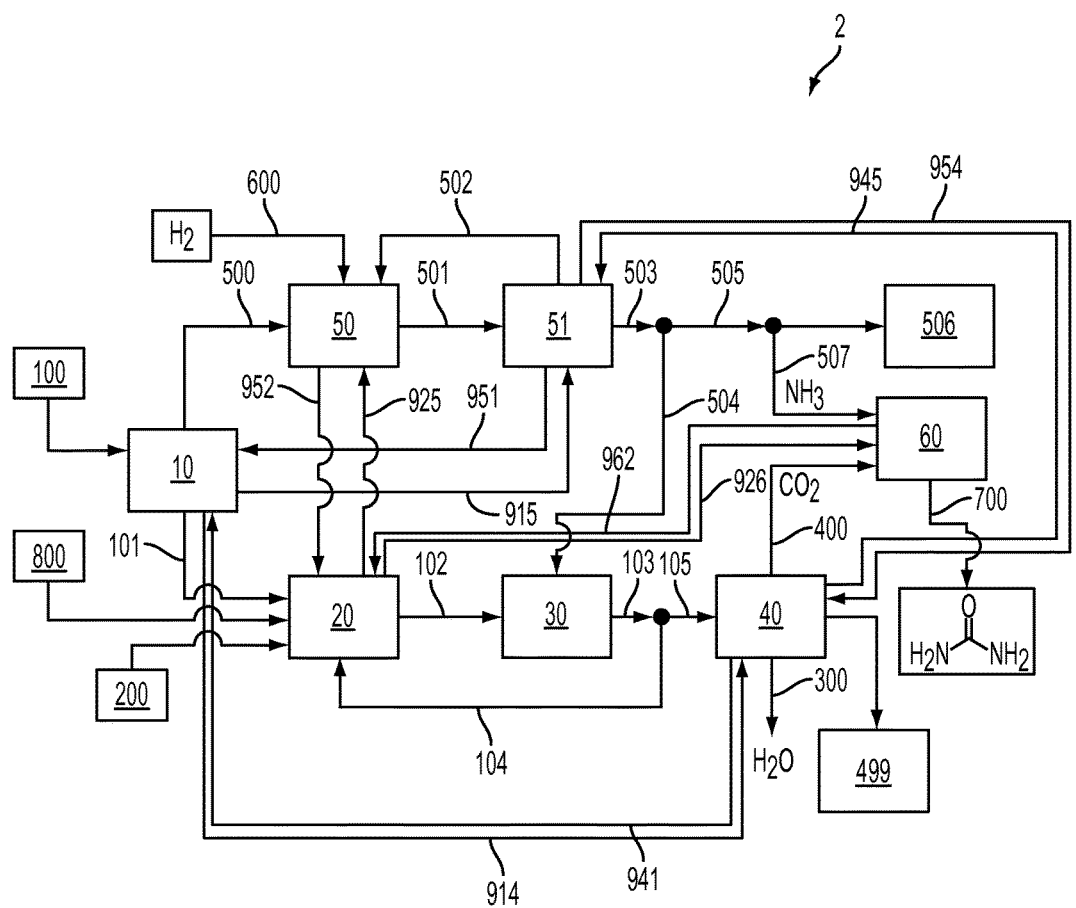
FIG. 2 is a schematic representation of an oxycombustion system with thermally integrated ammonia synthesis and including a urea synthesis unit, according to embodiments described herein.

Referring to FIG. 2, the oxycombustion system described above may additionally be configured as an integrated urea-synthesis oxycombustion system 2. The integrated urea-synthesis oxycombustion system 2 may include components of the oxycombustion system 1 of FIG. 1 and in addition may include a urea synthesis unit 60. When a urea synthesis unit 60 is present, the ammonia recovery stream 505 may be split, such that at least a portion of the ammonia in the ammonia recovery stream 505 is directed through a urea-precursor ammonia stream 507 into the urea synthesis unit 60. Any remaining ammonia not required by the urea synthesis unit 60 may be directed from the ammonia recovery stream 505 to ammonia recovery outlet 506. The urea-precursor ammonia stream 507 may then be combined in the urea synthesis unit 60 with $CO_2$ from the carbon dioxide recovery stream 400 to form urea that may be recovered from a urea recovery stream 700. The urea may be formed in the urea synthesis unit 60 using any well known process parameters, which typically may involve elevated temperatures such as from 150° C. to 250° C., for example and elevated pressures such as from 12 MPa to 40 MPa, for example. During urea synthesis, typically two molar parts of ammonia combine with one molar part of $CO_2$ to form an ammonium carbamate such as $H_2N$—CO—$ONH_4$, which is then dehydrated to yield urea and water. Urea formed by this reaction may be an aqueous solution or a melt that can be subjected to further processing such as prilling, granulation, pelletizing, or compacting. It should be understood that the integrated urea-synthesis oxycombustion system 2 of FIG. 2 may additionally require the implementation of process apparatus such as compressors, recirculation fans, pumps, and controllers using configurations that should be readily apparent to those having ordinary skill in the art, even though they may not be explicitly shown in FIG. 2.

In some embodiments, the integrated urea-synthesis oxycombustion system 2 may further include an air-separator capture-unit thermal linkage 914, 941, an ammonia-separator capture-unit thermal linkage 945, 954, or both, as described above with respect to the oxycombustion system 1 of FIG. 1. In further embodiments, the integrated urea-synthesis oxycombustion system 2 with or without the air-separator capture-unit thermal linkage 914, 941, an ammonia-separator capture-unit thermal linkage 945, 954 may also include a urea synthesis thermal integration such as a urea synthesis thermal linkage 926, 962 between the urea synthesis unit 60 and the oxycombustion reactor 10. With the urea-synthesis thermal linkage 926, 962 in place, excess heat from the oxycombustion reactor 10 may be used as an energy source for bringing the ammonia in the urea-precursor ammonia stream 507 and the carbon dioxide from the carbon dioxide recovery stream 400 up to a reaction temperature that facilitates or enables their reaction to form urea. Thereby, any contemplated additional heating unit at the urea synthesis unit 60 may be designed to use less energy or may even be eliminated entirely. The urea synthesis thermal linkage 926, 962 may be configured as any industrially feasible thermal-transfer loop that can bring about the desired transfer of heat from the oxycombustion reactor 10 to the urea synthesis unit 60. Such a thermal-transfer loop may contain a heat transfer fluid with appropriate thermal properties such as boiling point, for example. Thermal transfer to and from the thermal-transfer loop may be accomplished by any practical means such as through heat exchanger fins or coils. The heat transfer fluid in the separator loop may be circulated within the thermal-transfer loop by any practical means, such as with a pump, for example.

Figure 3:
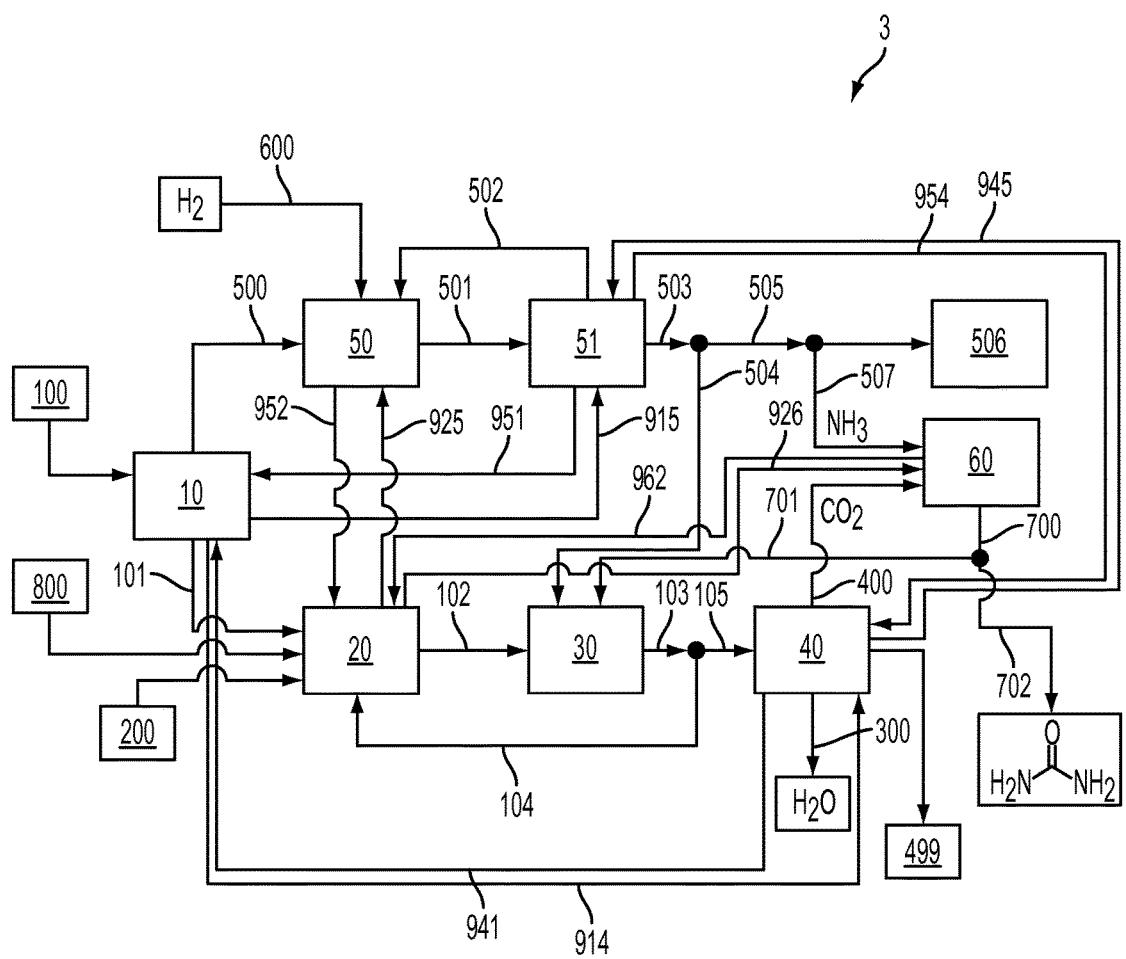
FIG. 3 is a schematic representation of an oxycombustion system with thermally integrated ammonia synthesis and including a urea synthesis unit, according to embodiments described herein, in which urea, ammonia, or both are used by the oxycombustion system to remove pollutants from flue gas generated in the oxycombustion reactor.

Referring to FIG. 3, the integrated urea-synthesis oxycombustion system 2 described above may be further configured as a urea flue-gas treatment system 3. The urea flue-gas treatment system 3 may include components of the oxycombustion system 1 and the integrated urea-synthesis oxycombustion system 2 and, in addition, the urea recovery stream 700 may be modified or added to. In one embodiment, the urea recovery stream 700 may be directed entirely to a urea scrubbing stream 701 that adds urea into the flue-gas treatment system 30 for use in scrubbing technologies that use urea to remove pollutants. In such embodiments, the urea from the urea scrubbing stream 701 may be used in addition to or in place of ammonia from the ammonia scrubbing stream 504. That is, at least one of the urea scrubbing stream 701 and the ammonia scrubbing stream 504 may be in fluidic communication with the flue-gas treatment system 30, such that at least a portion of the ammonia from the purified ammonia stream 503 or at least a portion of the urea from the urea recovery stream 700, or both, may be used to remove pollutants from the flue gas in the flue-gas treatment system 30. In other embodiments, a first portion of the urea recovery stream 700 may be directed to the urea scrubbing stream 701 while a second portion of the urea recovery stream 700 may be directed to a urea collection stream 702, such that any urea that is not required by the operation of the flue-gas treatment system 30 may be used for other purposes outside the urea flue-gas treatment system 3. It should be understood that the urea flue-gas treatment system 3 of FIG. 3 may additionally require the implementation of process apparatus such as compressors, recirculation fans, pumps, and controllers using configurations that should be readily apparent to those having ordinary skill in the art, even though they may not be explicitly shown in FIG. 3.

In some embodiments, the urea flue-gas treatment system 3 may further include an air-separator capture-unit thermal linkage 914, 941, an ammonia-separator capture-unit thermal linkage 945, 954, a urea synthesis thermal linkage 926, 962, any combination of two of these, or all of these, each as described above with respect to the oxycombustion system 1 of FIG. 1 or the integrated urea-synthesis oxycombustion system 2 of FIG. 2.

Thus, various embodiments of the oxycombustion system 1 of FIG. 1, the integrated urea-synthesis oxycombustion system 2 of FIG. 2, and the urea flue-gas treatment system 3 of FIG. 3 have been described. These systems make efficient use not only of nitrogen and oxygen components of air to simultaneously feed ammonia synthesis, oxycombustion, and, optionally, urea synthesis, but also in some embodiments use the ammonia and/or urea to clean flue gases that result from the oxycombustion. When ammonia and/or urea are generated in an integrated system, it is not necessary to procure the ammonia and/or urea from external sources when they are required or desired for use in scrubbing flue gas and removing pollutants from the flue gas. Additionally, the systems make efficient use of thermal energy through their at least one thermal integration such as a reactor thermal linkage of the ammonia synthesis unit with the oxycombustion reactor, a separator thermal linkage of the air separation unit with the ammonia separation unit, or both. Thermal integrations in this manner can eliminate needs in the oxycombustion systems for additional components such as refrigeration systems to condense ammonia or heaters to heat hydrogen and nitrogen in for ammonia synthesis, thereby potentially lowering an overall carbon footprint of the oxycombustion systems according to embodiments herein, as compared to separate combustion, ammonia synthesis, and urea synthesis systems without any thermal integration.

Having described above several embodiments of the oxycombustion systems, various embodiments of methods for performing oxycombustion with thermally integrated ammonia synthesis will now be described. In some embodiments, the methods for performing oxycombustion with thermally integrated ammonia synthesis may be performed using the oxycombustion system 1 of FIG. 1, the integrated urea-synthesis oxycombustion system 2 of FIG. 2, or the urea flue-gas treatment system 3 of FIG. 3 according to embodiments described above.

Referring generally to FIGS. 1-3 with regard to components of oxycombustion systems 1, 2, 3 that may be applicable to the embodiments of methods described below, the methods for performing oxycombustion with thermally integrated ammonia synthesis may include separating an air feed stream 100 with an air separation unit 10 into an oxygen stream 101 and a nitrogen stream 500. The oxygen stream 101 may be flowed to an oxycombustion reactor 20, and the nitrogen stream 500 may be flowed to an ammonia synthesis unit 50. The nitrogen stream 500 in the ammonia synthesis unit 50 may be combined with a hydrogen feed stream 600 to synthesize ammonia and form a crude ammonia stream 501 containing the ammonia and, optionally, unreacted nitrogen or hydrogen. The crude ammonia stream 501 may be condensed in an ammonia separation unit 51 so as to separate the ammonia in the crude ammonia stream 501 from any unreacted nitrogen or hydrogen in the crude ammonia stream 501 and form a purified ammonia stream 503. The methods may further include combining a fuel from a fuel feed stream 200 with the oxygen stream 101 from the air separation unit 10 to form a fuel mixture. The fuel mixture may be combusted in the oxycombustion reactor 20 to generate combustion heat, which optionally may be transferred for direct external use or to water to produce hot water or steam. The methods may further include transferring thermal energy through at least one thermal integration while the fuel mixture is being combusted and the ammonia is being synthesized. The at least one thermal integration may be chosen from a reactor thermal linkage of the ammonia synthesis unit with the oxycombustion reactor, a separator thermal linkage of the air separation unit with the ammonia separation unit, or both.

The air feed stream 100 may be separated by the air separation unit 10 using any method applicable to the type of air separation unit 10 employed in the oxycombustion systems 1, 2, 3. In exemplary embodiments, the air feed stream 100 may be separated by the air separation unit 10 by cryogenic distillation, by pressure-swing adsorption, by vacuum-swing adsorption, or a membrane technology, all of which are within the grasp of the person having ordinary skill in the art. The oxygen stream 101 may contain pure oxygen or substantially pure oxygen, such as from 80% to 100% by volume $O_2$ or from 90% to 100% by volume $O_2$ or from 90% to 99% by volume $O_2$, for example. Likewise, the nitrogen stream may contain pure nitrogen or substantially pure nitrogen such as from 80% to 100% by volume $N_2$ or from 90% to 100% by volume $N_2$ or from 90% to 99% by volume $N_2$, for example.

The methods for performing oxycombustion with thermally integrated ammonia synthesis may further include flowing the oxygen stream 101 to the oxycombustion reactor 20. To flow the oxygen stream 101 to the oxycombustion reactor 20, the oxygen stream 101 may be pressurized with a pump or compressor, for example.

The methods for performing oxycombustion with thermally integrated ammonia synthesis may further include flowing the nitrogen stream 500 to the ammonia synthesis unit 50. The nitrogen stream 500 may also be pressurized with a compressor or other suitable apparatus, for example, for injection into the ammonia synthesis unit 50.

The methods for performing oxycombustion with thermally integrated ammonia synthesis may further include combining the nitrogen stream 500 in the ammonia synthesis unit 50 with a hydrogen feed stream 600 to synthesize ammonia and form a crude ammonia stream 501 containing the ammonia and, optionally, unreacted nitrogen or hydrogen. Synthesizing the ammonia may additionally include raising the temperature of the mixture of nitrogen and hydrogen in the ammonia synthesis unit to a reaction temperature, pressurizing the mixture of nitrogen and hydrogen to a reaction pressure, or both. In general, suitable reaction pressures and reaction temperatures for ammonia synthesis may depend on a number of factors such as the configuration and construction materials of the ammonia synthesis unit 50, and optionally, the presence or absence of any reaction modifiers such as catalysts that may be added to the ammonia synthesis unit 50. In a non-limiting exemplary embodiment, a suitable reaction temperature for the ammonia synthesis may be from 300° C. to 550° C., and a suitable reaction pressure for the ammonia synthesis may be from 15 MPa to 25 MPa. It should be understood that other reaction temperatures and reaction pressures may be suitable, and that the selection of such reaction temperatures and reaction pressures is well within the grasp of the skilled artisan.

The methods for performing oxycombustion with thermally integrated ammonia synthesis may further include condensing at least a portion of the crude ammonia stream 501 in the ammonia separation unit 51. In some embodiments, only the ammonia in the crude ammonia stream 501 is condensed by cooling the crude ammonia stream to a temperature below the boiling point of ammonia, such as below −33° C., for example. The liquefied ammonia may then be separated from the unreacted nitrogen or hydrogen to form the purified ammonia stream 503.

The methods for performing oxycombustion with thermally integrated ammonia synthesis may further include combining a fuel from a fuel feed stream 200 with the oxygen stream 101 to form a fuel mixture, then combusting the fuel mixture in the oxycombustion reactor 20 to generate combustion heat. The fuel mixture may be formed either inside the oxycombustion reactor 20 or outside the oxycombustion reactor 20.

The methods for performing oxycombustion with thermally integrated ammonia synthesis may further include transferring thermal energy such as heat through at least one thermal integration of the oxycombustion system 1, 2, 3 while the fuel mixture is being combusted in the oxycombustion reactor 20 and the ammonia is being synthesized in the ammonia synthesis unit 50. The at least one thermal integration may be chosen from a reactor thermal linkage 925, 952 of the ammonia synthesis unit 50 with the oxycombustion reactor 20, a separator thermal linkage 915, 951 of the air separation unit 10 with the ammonia separation unit 51, or both.

In some embodiments in which the at least one thermal integration includes a reactor thermal linkage 925, 952, the reactor thermal linkage 925, 952 may be configured as a boiler loop that transfers heat to the ammonia synthesis unit 50 from the oxycombustion reactor 20 itself (for example, from a chamber in the oxycombustion reactor 20), from flue gas formed in the oxycombustion reactor 20, from hot water or steam that has been heated by combustion heat from the oxycombustion reactor 20, or a combination of any of these. The transferring of the thermal energy may then include circulating a heat transfer fluid through the boiler loop while the fuel mixture is being combusted and the ammonia is being synthesized. The heat transfer fluid for the boiler loop may be a fluid such as a gas or liquid, for example water or steam.

In some embodiments in which the at least one thermal integration includes a separator thermal linkage 915, 951 of the air separation unit 10 with the ammonia separation unit 51, the separator thermal linkage 915, 951 may be configured as a separator loop that transfers heat to the air separation unit from the ammonia separation unit. The transferring the thermal energy may then include circulating a heat transfer fluid through the separator loop while the fuel mixture is being combusted and the ammonia is being synthesized. The heat transfer fluid for the separator loop may be a fluid, such as a gas or liquid, with an appropriate boiling point and freezing point to enable the heat transfer fluid to circulate around the separator loop freely.

In some embodiments, the at least one thermal integration may include both a reactor thermal linkage 925, 952 of the ammonia synthesis unit 50 with the oxycombustion reactor 20 and a separator thermal linkage 915, 951 of the air separation unit 10 with the ammonia separation unit 51. As in the embodiments described above, the reactor thermal linkage 925, 952 may be configured as a boiler loop and the separator thermal linkage 915, 951 may be configured as a separator loop. In such embodiments, the transferring of the thermal energy may include both circulating a first heat transfer fluid through the boiler loop and circulating a second heat transfer fluid through the separator loop while the fuel mixture is being combusted and the ammonia is being synthesized.

In some embodiments, the methods for performing oxycombustion with thermally integrated ammonia synthesis may further include transferring thermal energy such as heat through at least one additional thermal integration of the oxycombustion system 1, 2, 3 in addition to the reactor thermal linkage 925, 952 of the ammonia synthesis unit 50 with the oxycombustion reactor 20, the separator thermal linkage 915, 951 of the air separation unit 10 with the ammonia separation unit 51, or both. The at least one additional thermal integration may include an air-separator capture-unit thermal linkage 914, 941 between the air separation unit 10 and the carbon dioxide capture unit 40, an ammonia-separator capture-unit thermal linkage 945, 954 between the ammonia separation unit 51 and the carbon dioxide capture unit 40, a urea synthesis thermal linkage 926, 962 between the urea synthesis unit 60 and the oxycombustion boiler 20, any combination of two of these, or all of these, each as described above with respect to the oxycombustion system 1 of FIG. 1 the integrated urea-synthesis oxycombustion system 2 of FIG. 2, or the urea flue-gas treatment system 3 of FIG. 3. The transference of thermal energy in any of these thermal integrations may include circulating a heat transfer fluid through a heat-transfer loop that serves as the respective thermal linkage.

The methods for performing oxycombustion with thermally integrated ammonia synthesis may further include treating in a flue-gas treatment system 30 a flue gas formed by the combustion of the fuel in the oxycombustion reactor 20. The treating of the flue gas may include removing pollutants from the flue gas and may also include using at least a portion of the ammonia in the purified ammonia stream 503, such as from the ammonia scrubbing stream 504 to remove the pollutants from the flue gas.

In some embodiments, the flue-gas treatment system 30 used to treat the flue gas formed by the combustion of the fuel in the oxycombustion reactor 20 outputs carbon dioxide. In such embodiments, the methods for performing oxycombustion with thermally integrated ammonia synthesis may further include capturing the carbon dioxide in a carbon dioxide capture unit 40 such as by cooling scrubbed flue gas from the flue-gas treatment system 30 until water present in the scrubbed flue gas condenses and the $CO_2$ is left in the gaseous state, for example.

In some embodiments, at least a portion of any carbon dioxide captured in the carbon dioxide capture unit 40 may be combined with the ammonia in the purified ammonia stream 503 to form a urea reactant mixture. The methods may then include synthesizing urea from the urea reactant mixture in a urea synthesis unit 60 (FIGS. 2 and 3), for example. The methods may also include pressurizing the ammonia, the $CO_2$, or the urea reactant mixture to from 12 MPa to 40 MPa, for example, and heating the ammonia, the $CO_2$, or the urea reactant mixture to from 150° C. to 250° C. to enable the urea synthesis reaction to commence or be maintained.

In some embodiments, the methods for performing oxycombustion with thermally integrated ammonia synthesis may further include treating the flue gas in the flue-gas treatment system 30, and treating the flue gas may include using at least a portion of the ammonia from the purified ammonia stream 503, at least a portion of the urea in the urea recovery stream 700 (see FIG. 3), or both, to remove the pollutants from the flue gas. In such embodiments, the flue-gas treatment system 30 may include technologies, as described above, for removing $NO_R$, $SO_x$, particulates, and other impurities with the aid of ammonia, urea, or both.

Thus, various embodiments of methods for performing oxycombustion with thermally integrated ammonia synthesis have been described. The methods may be performed using the oxycombustion system 1 of FIG. 1, the integrated urea-synthesis oxycombustion system 2 of FIG. 2, the urea flue-gas treatment system 3 of FIG. 3, modifications thereof, or other suitable oxycombustion systems. These methods make efficient use not only of nitrogen and oxygen components of air to simultaneously feed ammonia synthesis, oxycombustion, and, optionally, urea synthesis, but also in some embodiments use the ammonia and/or urea to clean flue gases that result from the oxycombustion. When ammonia and/or urea are generated in an integrated system, it is not necessary to procure the ammonia and/or urea from external sources when they are required or desired for use in scrubbing flue gas and removing pollutants from the flue gas. Additionally, by employing the systems according to embodiments herein, the methods make efficient use of thermal energy through the at least one thermal integration in the oxycombustion systems, such as a reactor thermal linkage of the ammonia synthesis unit with the oxycombustion reactor, a separator thermal linkage of the air separation unit with the ammonia separation unit, or both. Thermal integrations in this manner can eliminate needs in the oxycombustion systems for additional components such as refrigeration systems to condense ammonia or heaters to heat hydrogen and nitrogen in for ammonia synthesis, thereby potentially lowering an overall carbon footprint of the oxycombustion systems according to embodiments herein, as compared to separate combustion, ammonia synthesis, and urea synthesis systems without any thermal integration.

It should be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

What is claimed is:

1. A thermally-integrated oxycombustion system comprising:
   an air separation unit that separates an air feed stream into an oxygen stream and a nitrogen stream;
   an ammonia synthesis unit that synthesizes ammonia from a hydrogen feed stream and the nitrogen stream from the air separation unit to form a crude ammonia stream containing the ammonia and, optionally, unreacted nitrogen and hydrogen;
   an ammonia separation unit that condenses at least a portion of the crude ammonia stream formed in the ammonia synthesis unit and separates the ammonia from unreacted nitrogen and hydrogen to form a purified ammonia stream;
   an oxycombustion reactor that combusts a fuel from a fuel feed stream in the presence of the oxygen stream from the air separation unit to produce combustion heat;
   a flue-gas treatment system that treats a flue gas formed by the combustion of the fuel in the oxycombustion reactor with ammonia separated in the ammonia separation unit to remove pollutants from the flue gas and output carbon dioxide;
   a carbon dioxide capture unit that captures the carbon dioxide generated in the flue-gas treatment system; and
   a plurality of thermal integrations comprising:
      a reactor thermal linkage of the ammonia synthesis unit and the oxycombustion reactor;
      a separator thermal linkage of the air separation unit and the ammonia separation unit;
      an air-separator capture-unit thermal linkage of the air separation unit and the carbon dioxide capture unit directing heat from the air separation unit to the carbon dioxide capture unit; and
      an ammonia-separator capture-unit thermal linkage of the ammonia separation unit and the carbon dioxide capture unit directing heat from the ammonia separation unit to the carbon dioxide capture unit.

2. The thermally-integrated oxycombustion system of claim 1, wherein the reactor thermal linkage of the ammonia synthesis unit with the oxycombustion reactor comprises a boiler loop that transfers combustion heat to the ammonia synthesis unit from the oxycombustion reactor, from flue gas formed in the oxycombustion reactor, from hot water or steam that has been heated from the combustion heat, or a combination thereof.

3. The thermally-integrated oxycombustion system of claim 1, wherein the separator thermal linkage of the air separation unit with the ammonia separation unit comprises a separator loop that transfers heat to the air separation unit from the ammonia separation unit.

4. The thermally-integrated oxycombustion system of claim 1, wherein the purified ammonia stream is in fluidic communication with the flue-gas treatment system and at least a portion of the ammonia separated in the ammonia separation unit is used in the flue-gas treatment system to remove the pollutants from the flue gas.

5. The thermally-integrated oxycombustion system of claim 1, further comprising a urea synthesis unit that synthesizes urea to produce a urea stream from carbon dioxide captured in the carbon dioxide capture unit and the ammonia in the purified ammonia stream.

6. The thermally-integrated oxycombustion system of claim 5, wherein at least one of the urea stream and the purified ammonia stream is in fluidic communication with the flue-gas treatment system and at least a portion of the ammonia in the purified ammonia stream or at least a portion of the urea in the urea stream, or both, is used to remove pollutants from the flue gas in the flue-gas treatment system.

7. The oxycombustion system of claim 5, further comprising a urea synthesis thermal linkage of the urea synthesis unit and the oxycombustion reactor.

8. The thermally-integrated oxycombustion system of claim 7, wherein:
   both the purified ammonia stream and the urea stream and are in fluidic communication with the flue-gas treatment system; and
   both ammonia in the purified ammonia stream and urea in the urea stream are used to remove pollutants from the flue gas in the flue-gas treatment system.

* * * * *

UNITED STATES PATENT AND TRADEMARK OFFICE
CERTIFICATE OF CORRECTION

PATENT NO. : 10,106,430 B2
APPLICATION NO. : 14/143737
DATED : October 23, 2018
INVENTOR(S) : Mourad Younes and Tidjani Niass Page 1 of 1

It is certified that error appears in the above-identified patent and that said Letters Patent is hereby corrected as shown below:

Column 16, Line 36, Claim 8:
"both the purified ammonia stream and the urea stream and"
Should read:
--both the purified ammonia stream and the urea stream--.

Signed and Sealed this
Twelfth Day of February, 2019

Andrei Iancu
*Director of the United States Patent and Trademark Office*